US009073818B2

(12) United States Patent
Herrwerth et al.

(10) Patent No.: US 9,073,818 B2
(45) Date of Patent: Jul. 7, 2015

(54) QUATERNARY DIALKANOLAMINE ESTERS (75) Inventors: Sascha Herrwerth, Essen (DE); Burghard Gruening, Essen (DE); Hans-Juergen Koehle, Mainhausen (DE); Isabella Ulrich-Brehm, Ratingen (DE)

(73) Assignee: EVONIK DEGUSSA GMBH, Essen (DE)

( * ) Notice: Subject to any disclaimer, the term of this patent is extended or adjusted under 35 U.S.C. 154(b) by 10 days.

(21) Appl. No.: 13/701,815

(22) PCT Filed: May 2, 2011

(86) PCT No.: PCT/EP2011/056924
§ 371 (c)(1),
(2), (4) Date: Dec. 3, 2012

(87) PCT Pub. No.: WO2011/151119
PCT Pub. Date: Dec. 8, 2011

(65) Prior Publication Data
US 2013/0078208 A1  Mar. 28, 2013

(30) Foreign Application Priority Data

Jun. 2, 2010  (DE) .................. 10 2010 029 606

(51) Int. Cl.
| A61K 31/74 | (2006.01) |
| A61K 8/73 | (2006.01) |
| A01N 37/02 | (2006.01) |
| C11D 3/00 | (2006.01) |
| C07C 219/08 | (2006.01) |
| A61K 8/41 | (2006.01) |
| A61Q 5/02 | (2006.01) |
| A61Q 5/12 | (2006.01) |
| A61Q 19/10 | (2006.01) |
| C07C 213/06 | (2006.01) |
| C11D 1/62 | (2006.01) |
| A61Q 19/00 | (2006.01) |
| C11D 3/30 | (2006.01) |

(52) U.S. Cl.
CPC .............. *C07C 219/08* (2013.01); *A61K 8/416* (2013.01); *A61Q 5/02* (2013.01); *A61Q 5/12* (2013.01); *A61Q 19/10* (2013.01); *C07C 213/06* (2013.01); *C11D 1/62* (2013.01); *C11D 3/001* (2013.01); *C11D 3/0015* (2013.01); *A61Q 19/00* (2013.01); *C11D 3/30* (2013.01)

(58) Field of Classification Search
None
See application file for complete search history.

(56) References Cited

U.S. PATENT DOCUMENTS

2004/0258651 A1  12/2004 Pascaly et al.
2011/0237667 A1*  9/2011 Loeffler et al. ............... 514/547

FOREIGN PATENT DOCUMENTS

| DE | 411966 | 4/1925 | |
| DE | 43 08 794 C1 | 4/1994 | |
| DE | 103 27 871 A1 | 1/2005 | |
| DE | 10 2008 015 899 A1 * | 9/2008 | ............... A61K 8/41 |
| DE | WO 2009/018955 A2 * | 2/2009 | ............... A61K 8/41 |
| DE | 10 2008 001 788 A1 | 11/2009 | |
| EP | 0483195 A | 5/1992 | |
| EP | 0 643 128 A1 | 3/1995 | |
| JP | H04-333667 A | 11/1992 | |
| JP | H05-195432 A | 8/1993 | |
| JP | 6-228877 | 8/1994 | |
| JP | 2000-327544 A | 11/2000 | |
| JP | 2002-155469 A | 5/2002 | |
| JP | 2002212038 | 7/2002 | |
| JP | 2008-291007 A | 12/2008 | |
| WO | WO9101295 | 2/1991 | |
| WO | 2009/018955 A2 | 2/2009 | |

OTHER PUBLICATIONS

Solodin et al.; "Synthesis of Amphiphilic Derivatives of N-Methyldiethanolamine Cationic Lipids 5"; Synlett; Issue 7; p. 620 (1996).*
Lagerman, R., et al., "Synthesis and Performance of Ester Quaternary Biodegradable Softners", JAOCS, Jan. 1994, pp. 97-100, vol. 71, No 1.
Shapiro, I., et al., "Environmentally Friendly Ester Quats", Cosmetics & Toiletries magazine, Dec. 1994, vol. 109, pp. 77-80.
Puchta, R. et al., "A New Generation of Softners", Tenside Surf. Det., May 1993, vol. 30, No. 3, pp. 186-191.
Brock, M. et al., "A New Generation of Softners", Tenside Surf. Det., May 1993, vol. 30, No. 3, pp. 394-399.
Schrader, K. et al., "Grundlagen und Rezepturen der Kosmetika" ["Principles and Formulations of Cosmetics"], 1989, 2nd edition, p. 329 to 341, Hüthig Buch Verlag Heidelberg.
Abstract of WO2009/138306 A1, dated Nov. 19, 2009 (corresponding to DE102008001788 A1).
International Search Report dated Jul. 28, 2011 issued in PCT/EP2011/056924 (previously submitted on Dec. 3, 2012).
English-language translation of a Japanese Official Action dated Mar. 3, 2015 received in related Japanese Patent Application No. JP 2013-512806.

* cited by examiner

*Primary Examiner* — Jeffrey T Palenik
(74) *Attorney, Agent, or Firm* — Scully, Scott, Murphy & Presser, P.C.

(57) ABSTRACT

The invention relates to novel quaternary ammonium compounds of the esterquat type, to a method for the production thereof, and to the use thereof in formulations.

19 Claims, 2 Drawing Sheets

QUATERNARY DIALKANOLAMINE ESTERS

FIELD OF THE INVENTION

The present invention provides novel quaternary ammonium compounds of the ester quat type, and a process for preparation thereof, and also the use thereof in formulations.

STATE OF THE ART

In the past, quaternary ammonium compounds ("quats") in the form of monoalkyl and dialkyl quats having one or two long alkyl chains in the molecule respectively found wide use in various fields of application. These include fabric softeners for textiles, antistatic formulations, cleaning compositions, skincare compositions, hair conditioners and corrosion inhibitors, printing ink removers for paper and many others.

In the field of skincare compositions, the monoalkyl quats used on a large scale in industry include, for example, Cetrimonium Chloride (INCI) (for example commercially available as VARISOFT® 300, Evonik Goldschmidt GmbH) and Behentrimonium Chloride (INCI) (for example commercially available as VARISOFT® BT 85 pellets, Evonik Goldschmidt GmbH), and the dialkyl quats used include Dicetyldimonium Chloride (INCI) (for example commercially available as VARISOFT® 432 PPG, Evonik Goldschmidt GmbH).

As well as their good properties as conditioners, these alkylammonium cations, however, also have some disadvantages. These include inadequate biodegradability and unfavorable ecotoxicological properties.

Particularly in the field of skincare and haircare compositions, alongside the conventional alkyl quats, what are called the ester quats have also become established over the years, for example Distearoylethyl Dimonium Chloride (INCI), commercially available as VARISOFT® EQ 65 pellets (Evonik Goldschmidt GmbH) or Distearoylethyl Hydroxyethylmonium Methosulfate (INCI), commercially available as Dehyquart F 75 (Cognis).

The generic term "ester quat" is generally understood to mean di- or trialkanolamines esterified with fatty acids, in the salt form thereof.

These quaternized fatty acid alkanolamine ester salts are known substances which can be obtained by appropriate methods of preparative organic chemistry. Typically, the preparation of the ester quats is based on a multistage process, in which reaction of an alkanolamine with carboxylic acids or corresponding derivatives is first used to prepare the esterified tertiary alkanolamine, which is then subsequently quaternized with a suitable reagent.

In this context, reference is made to EP0483195, according to which triethanolamine is partially esterified with fatty acids in the presence of hypophosphorus acid, air is passed through and then quaternization is effected with dimethyl sulfate or ethylene oxide. The compounds cited therein serve as softeners for textiles.

DE4308794 describes the preparation of solid ester quats, by performing the quaternization of the triethanolamine esters in the presence of suitable dispersants, preferably fatty alcohols.

Reviews on this topic can be found, for example, in R. Puchta et al. in Tens. Surf. Det., 30, 186 (1993), M. Brock in Tens. Surf. Det., 30, 394 (1993), R. Lagerman et al. in J. Am. Chem. Soc., 71, 97 (1994) or in I. Shapiro in Cosm. Toil., 109, 77 (1994).

Compared to alkyl quats, ester quats have a more favorable profile of ecotoxicological characteristics and also have, due to the presence of the ester bond, an improvement in biodegradability over alkyl quats.

The environmental compatibility of formulations and ingredients thereof is becoming ever more important, firstly due to corresponding legislation, but particularly as a result of a change in consumer awareness. The consumer is placing ever greater value on products which do not have an adverse effect on the environment. As a result, properties such as ecotoxicity or biodegradability are moving ever more into the center of public attention.

Good biodegradability is ensured by the conversion of the substances by biological processes, which typically proceed in wastewater treatment. The fragments which form have an even lower risk of environmental damage than the starting materials and are very easy to handle in the conventional processes for treatment of wastewater and solid waste. In the case of inadequate biodegradability, the functioning of aquatic communities can be impaired over the course of time.

Numerous softeners or conditioners currently available on the market, the biodegradability of which has already been improved, however, decline in efficacy compared to the conventional products.

For example, the application properties of the ester quats currently available are likewise at a high level, but cannot keep up with the application properties of Behentrimonium Chloride (INCI) in the case of prolonged rinse times. The desired conditioning properties are reduced more rapidly as a result of the rinse process in the case of the prior art ester quats. Since conventional products to date have either lacked effective performance or good environmental compatibility, there is still a high demand for compounds which cover both areas, by combining excellent properties as care products and high environmental compatibility in one.

In the haircare sector, conditioners play an important role. Their task is to protect the hair and to remedy existing damage.

A large amount of damage to the hair results from the fact that the hair is exposed daily to various environmental stress factors, including temperature, humidity, sunlight or air pollution. In addition, chemical hair treatments such as bleaching, coloring, tinting, straightening, or the use of permanent waves, lead to adverse effects on the hair structure.

For example, in the case of a permanent wave, both the cortex and the cuticle of the hair are attacked. The disulfide bridges of cystine are broken up by the reduction step and partly oxidized to cysteic acid in the subsequent oxidation step.

Bleaching not only destroys melanin, but also oxidizes approx. 15 to 25% of the disulfide bonds of cystine in the case of mild bleaching. In the case of excessive bleaching, there may even be up to 45% oxidation (K. F. de Polo, A Short Textbook of Cosmetology, 2000, Verlag für chemische Industrie, H. Ziolkowsky GmbH).

And even the daily washing, combing and blow-drying of the hair leaves traces. The unwanted consequences are manifested, for example, in a rough hair surface, reduced mechanical stability and a rise in electrostatic charge. Broken hairs, the formation of split ends, combing difficulty and loss of natural shine are the result. Conditioners have the task of protecting the hair from these adverse effects, but should if possible not have an adverse effect on the environment.

For this purpose, the conditioner must be able to be absorbed onto the hair. Due to the anionic sites on the hair surface, based on protein structures, cationic compounds form a preferred product class among the conditioning agents, since they ensure the necessary affinity for the hair. In the case of existing hair damage, the number of anionic groups is actually increased due to the presence of oxidized protein structures, for example the abovementioned cysteic acid. Specifically in these damaged areas, cationic conditioners can display their full efficacy.

It was an object of the invention to remedy at least one disadvantage of the prior art or at least to reduce it, and more particularly to provide active ingredients which remain on the target surface even in the case of long rinse times and still display their effect.

DESCRIPTION OF THE INVENTION

It has been found that, surprisingly, the compounds of the general formula (I) according to claim 1 described hereinafter, a process for preparation thereof and the compositions and formulations described are capable of achieving the stated object.

The present invention therefore provides specific quaternary dialkanolamine esters.

The invention further provides a process for preparation thereof, and for the use thereof in formulations.

An advantage of the present invention is that the inventive compounds already display a good effect even in the case of small use amounts.

A further advantage is that the inventive compounds are not very troublesome from an ecological point of view.

Another advantage is that the inventive compounds on keratinic fibers exhibit an improvement in conditioning effect in the case of relatively long rinse times over quaternary ester compounds known to date.

A contribution to the solution of the problem stated at the outset is thus made by quaternary dialkanolamine esters of the general formula (I)

formula (I)

where
$Y^1$ and $Y^2$ are the same or different and are each independently an alkyl radical having 1 to 6 carbon atoms, a benzyl radical or H,
n=1 to 4
A- is an anion, preferably selected from the group comprising chloride, bromide, iodide, methylsulfate, tosylate, phosphate, sulfate, ethylsulfate, hydrogensulfate, lactate, acetate and citrate, preferably chloride and methylsulfate,
$X^1$ and $X^2$ are the same or different and are each independently selected from groups (a), (b), (c) and (d), these groups consisting of
(a) acyl radicals containing 6 to 14 carbon atoms,
(b) acyl radicals containing 15 to 20 carbon atoms and at least one carbon-carbon double bond,
(c) acyl radicals containing 20 to 24 carbon atoms and
(d) acyl radicals which contain 3 to 28 carbon atoms and are not included in groups (a) to (c), or H,
with the proviso that each molecule of the general formula (I) contains a numerical average of
0.30 to 1.50, preferably 0.35 to 1.00 and especially 0.40 to 0.90 radicals from group (a),
0.10 to 1.30 and especially 0.20 to 0.80 radicals from group (b),
0.40 to 1.60, preferably 0.50 to 1.50 and especially 0.80 to 1.40 radicals from group (c),
0 to 0.20, preferably 0.0010 to 0.10 and more preferably 0.0050 to 0.02 radical from group (d),
and
the numerical averages per molecule of the radicals from groups (a), (b), (c) and (d) add up to 2.

It is apparent to the person skilled in the art that the general formula (I) represents a mixture of various quaternary dialkanolamine esters.

The radical determining $Y^1$ and $Y^2$ is preferably a linear alkyl radical which is preferably unsubstituted, a benzyl radical or H; more particularly, the radical is selected from the group comprising, preferably consisting of, —$CH_3$, —$C_2H_5$, benzyl and H.

n is especially preferably 2.

The acyl radicals from groups (a) and (c) are preferably saturated.

The acyl radicals from groups (a), (b), (c) and (d) are especially those from the naturally occurring fatty acids with corresponding chain lengths.

They preferably thus contain even numbers of carbon atoms. Acyl radicals from group (a) are preferably selected from $C_5H_{11}CO$—, $C_7H_{15}CO$—, $C_9H_{19}CO$—, $C_{11}H_{23}CO$—, and $C_{13}H_{27}CO$—.

Since the use of technical lauric acid is particularly preferred, a particularly preferred acyl radical from group (a) is an acyl radical having a chain length of 12 carbon atoms. In this context, it is preferable that groups (b), (c) and (d) are correspondingly assigned 0 to 1% by weight and preferably 0.02 to 0.50% by weight of acyl radicals of a fatty acid having a chain length of less than 11 and preferably of 6 to 10 carbon atoms, and 0 to 1% by weight and preferably 0.30 to 0.70% by weight of acyl radicals of a fatty acid having a chain length of greater than 13 and preferably of 14 to 28 carbon atoms, the percentages by weight being based on the total amount of all acyl radicals which can be derived from the technical lauric acid.

Acyl radicals from group (b) are preferably selected from $C_{15}H_{29}CO$—, $C_{17}H_{33}CO$—, $C_{17}H_{31}CO$—, $C_{17}H_{29}CO$—, $C_{19}H_{37}CO$—, $C_{19}H_{31}CO$— and $C_{19}H_{29}CO$—, and from the acyl radicals of the monounsaturated fatty acids, especially of palmitoleic acid, petroselic acid, oleic acid, elaidic acid, vaccenic acid, gadoleic acid and eicosenoic acid, and from the acyl radicals of the polyunsaturated fatty acids, especially linoleic acid, α-/γ-linolenic acid, calendic acid, punicic acid and arachidonic acid.

Particularly preferred acyl radicals from group (b) are the acyl radicals from a technical oleic acid with corresponding chain lengths, especially the $C_{15}H_{29}CO$—, $C_{17}H_{33}CO$, $C_{17}H_{31}CO$—, $C_{17}H_{29}CO$— and $C_{19}H_{37}CO$— radicals in a weight ratio of 3-7:68-76:5-13:1-3:0-2. In this context, it is preferable that groups (a), (c) and (d) are correspondingly assigned 0 to 3% by weight and preferably 0.50 to 1.50% by weight of acyl radicals from a fatty acid having a chain length of 14 carbon atoms, 2 to 7% by weight and preferably 4 to 6% by weight of acyl radicals from a fatty acid having a chain length of 16 carbon atoms, and 0 to 3% by weight and preferably 0.50 to 1.50% by weight of acyl radicals from a fatty acid having a chain length of 18 carbon atoms, the percentages by weight being based on the total amount of all acyl radicals which can be derived from the technical oleic acid.

Acyl radicals from group (c) are preferably selected from $C_{19}H_{39}CO$—, $C_{21}H_{43}CO$— and $C_{23}H_{47}CO$—.

Particularly preferred acyl radicals from group (c) are the acyl radicals from a technical behenic acid with corresponding chain lengths, especially the $C_{19}H_{39}CO—$, $C_{21}H_{43}CO—$ and $C_{23}H_{47}CO—$ radicals in a weight ratio of 4-8:85-99:0-3. In this context, it is preferable that groups (a), (c) and (d) are correspondingly assigned 0 to 3% by weight and preferably 0.50 to 1.50% by weight of acyl radicals from a fatty acid having a chain length of less than 19, preferably 6 to 18 and especially 15 to 18 carbon atoms, 0 to 1% by weight and preferably 0.25 to 0.75% by weight of acyl radicals from a fatty acid having a chain length of 26 carbon atoms, the percentages by weight being based on the total amount of all acyl radicals which can be derived from the technical behenic acid.

The acyl radicals from group (d) are preferably determined by carboxylic acids which are additionally present in technical mixtures of the carboxylic acids which determine the acyl radical from groups (a), (b) and (c), these technical mixtures having been used for preparation of the inventive ester quats. For example, technical oleic acid (group (b)) also contains a small proportion of saturated fatty acids having a chain length of 18 carbon atoms, in which case the acyl radicals thereof should be assigned to group (d).

It is preferable in accordance with the invention that the numerical average of the molar ratio of the sum of acyl radicals from group (a) and group (b) to acyl radicals from group (c) in the inventive quaternary dialkanolamine esters of the general formula (I) is 1:0.67 to 4, especially 1:0.8 to 3.

Very particular preference is given to ester quats in which the acyl radicals of groups (a) to (d) are determined by the acyl radicals of a mixture consisting of technical lauric acid, especially EDENOR C1298-100 (Emery Oleochemicals), technical oleic acid, especially EDENOR Ti05 (Emery Oleochemicals) and technical behenic acid, especially EDENOR C2285 (Emery Oleochemicals).

The present invention provides a process for preparing the inventive quaternary dialkanolamine esters.

The inventive quaternary dialkanolamine esters are advantageously obtainable by the process described hereinafter.

The process according to the invention for preparing quaternary dialkanolamine esters comprises the process steps of
A) reacting, preferably esterifying, an alkyldialkanolamine in which the two alkanol groups are selected from the group consisting of —$CH_2OH$, —$C_2H_4OH$, —$C_3H_6OH$ and —$C_4H_8OH$, especially —$C_2H_4OH$, and the alkyl group is selected from the group consisting of alkyl radicals having 1-6 carbon atoms, especially linear alkyl radicals, which are preferably unsubstituted, with a mixture of carboxylic acids consisting of the groups of
(e) carboxylic acid containing 6 to 14 carbon atoms
(f) carboxylic acid containing 15 to 20 carbon atoms and at least one carbon-carbon double bond and
(g) carboxylic acid containing 20 to 24 carbon atoms and optionally
(h) carboxylic acid which contains 3 to 28 carbon atoms and is not included in groups (e), (f) and (g),
B) reacting, preferably quaternizing, the product from process step A) with a quaternizing agent selected from the group comprising, preferably consisting of, dialkyl sulfates, alkyl halides and benzyl halides and/or
C) neutralizing the reaction mixture with an acid, preferably an organic acid,
with the proviso that, based on all carboxylic acids from groups (e), (f), (g) and (h), 0 to 10 mol %, preferably 0.5 to 5 mol % and preferably 0.25 to 1.0 mol % of carboxylic acids from group (h) is used.

Alkyldialkanolamine used with particular preference in process step (a) is methyldiethanolamine.

The carboxylic acids from group (h) are preferably determined by the carboxylic acids which are additionally present in technical mixtures of the carboxylic acids from groups (e), (f) and (g) which are used in the process according to the invention.

Preferred alkyl halides used in process step B) have 1 to 6 carbon atoms, special preference being given here to methyl chloride; dialkyl sulfate preferred in this context is dimethyl sulfate.

Process steps A) and B) can be conducted under the customary process conditions known to those skilled in the art for esterification and quaternization respectively. In process step A), the alkyldialkanolamine is thus preferably heated here with a mixture of the fatty acids claimed at 140-200° C., optionally with additional use of an esterification catalyst, and water of condensation formed is distilled off continuously. To complete the reaction, vacuum is optionally applied, and the course of the reaction is monitored via the measurement of the acid number. Detailed instructions for this purpose can be found in DE4111966 inter alia.

In process step B), the alkyldialkanolamine ester is preferably reacted, optionally in solvent at 60-120° C., with the quaternizing reagent, more preferably with methyl chloride. In this case, the quaternizing reagent is used in excess; the pressure is regulated between 1-8 bar. Once the tertiary amine has been reacted down to the desired conversion, the excess of quaternizing reagent is removed by distillation. Detailed instructions for this purpose can be found in EP0643128 inter alia.

The carboxylic acids from groups (e), (f), (g) and (h) used with preference in the process according to the invention correspond to the carboxylic acids which give the preferred acyl radicals from groups (a), (b), (c) and (d) in the inventive compound.

Special preference is given here to the use of a mixture of carboxylic acids consisting of technical lauric acid, especially EDENOR C1298-100 (Emery Oleochemicals), technical oleic acid, especially EDENOR Ti05 (Emery Oleochemicals), and technical behenic acid, especially EDENOR C2285 (Emery Oleochemicals).

Organic acids used with preference in process step C) are selected from the group consisting of citric acid, tartaric acid, lactic acid, acetic acid, formic acid and glycolic acid.

The pH is adjusted in process step C) preferably to a pH of 3.5 to 5.5, preferably while stirring. This step is effected preferably at a temperature of especially 40-60° C.

Preference is given in accordance with the invention to using, in the process according to the invention, for each mole of alkyldialkanolamine,
0.30 to 1.50 mol, preferably 0.30 to 1.00 mol and especially 0.40 to 0.90 mol of carboxylic acid from group (e),
0.10 to 1.30 mol and especially 0.20 to 0.80 mol of carboxylic acid from group (f) and
0.40 to 1.60 mol, preferably 0.50 to 1.50 mol and especially 0.80 to 1.40 mol of carboxylic acid from group (g)

In this context, it is preferable in accordance with the invention that the molar ratio of the carboxylic acids used from the sum of groups (e) and (f) to group (g) is 1:0.67 to 4, especially 1:0.8 to 3.

A preferred process according to the invention is characterized in that for each mole of alkyldialkanolamine, carboxylic acids from groups (e), (f), (g) and optionally (h) are used in a total amount of 1.80 to 2.5 mol, more preferably 1.85 to 2.2 mol.

A process preferred in accordance with the invention is characterized in that in process step B) at least one solvent selected from the group consisting of short-chain alcohols, fatty alcohols, polyols and carbonates is used.

Short-chain alcohols in this context are those having a chain length of 2 to 6 carbon atoms, for example ethanol, butanol, isopropanol, hexanol. A fatty alcohol is understood in this context to mean an unbranched or branched monoalcohol having an alkyl group of 8 to 30 carbon atoms. Preferred fatty alcohols are lauryl alcohol, myristyl alcohol, cetyl alcohol, palmoleyl alcohol, stearyl alcohol, isostearyl alcohol, oleyl alcohol, elaidyl alcohol, petroselinyl alcohol, Guerbet alcohol, arachyl alcohol, gadoleyl alcohol, behenyl alcohol and erucyl alcohol and the technical mixtures thereof, preferably technical coconut or tallow fat alcohols having 12 to 18 and preferably 16 to 18 carbon atoms.

Alcohols used with preference are short-chain, especially isopropanol.

Polyols used in process step B) are especially ethylene glycol, propylene glycol, dipropylene glycol and butylene glycol; carbonate used is especially propylene carbonate and ethylene carbonate.

It is preferable that the solvent is used in an amount of 0.5 to 50% by weight and preferably 1 to 40% by weight, based on the sum of the weights of theoretically expected quaternary ester compound and solvent.

Detailed instructions for this purpose can be found in DE4308794.

The present invention further provides a composition comprising inventive quaternary dialkanolamine esters and/or quaternary dialkanolamine esters obtainable by the above-described process according to the invention, at least one solvent, especially selected from short-chain alcohols, fatty alcohols, polyols and carbonates, and optionally at least one carboxylic acid selected from at least one of groups (e), (f), (g) and (h).

The inventive composition preferably consists of the aforementioned components.

The solvent preferably accounts for 0.5 to 50% by weight and preferably 1-40% by weight, based on the total weight of the composition.

The solvents present in the inventive composition generally originate from the addition of solvents in process step B) of the process according to the invention, and so the preferred solvents mentioned in this context are preferably present in the inventive compositions. Thus, inventive compositions preferably comprise fatty alcohols, which are a mixture of various fatty alcohols selected from alcohols having a chain length of C12 to C24, more preferably a mixture of cetyl alcohol (C16) and stearyl alcohol (C18). Short-chain alcohol present with special preference is isopropanol. Polyols present with preference are especially ethylene glycol, propylene glycol, dipropylene glycol and butylene glycol; carbonate present with preference is especially propylene carbonate.

The carboxylic acids preferably account for 0% by weight to 10% by weight and preferably 0.01% by weight—3% by weight, based on the total weight of the composition.

The carboxylic acids present in the inventive composition generally originate from the carboxylic acids added in excess in process step A) of the process according to the invention, and so the preferred carboxylic acids mentioned in this context are preferably present in the inventive compositions.

The present invention further provides for the use of the inventive quaternary dialkanolamine esters and/or of the quaternary dialkanolamine esters obtainable by the process according to the invention and/or of at least one inventive composition for production of formulations, especially of cosmetic or pharmaceutical formulations and care and cleaning formulations for use in the domestic and industrial sector. In this context, preferred cosmetic or pharmaceutical formulations are especially skin and hair treatment formulations, especially hair conditioning formulations. Preferred care and cleaning formulations for use in the domestic and industrial sector in this context are textile care compositions, for example fabric softeners, and care compositions for hard surfaces, especially for land vehicles, water vehicles, aircraft, window panes and sills, shower enclosures, floors such as carpets, tiles, laminates, parquet, cork floors, marble, stone and stoneware floors, domestic ceramics such as WCs, washbasins, bidets, shower trays, bathtubs, doorknobs, fittings, domestic appliances such as washing machines, dryers, machine dishwashers, ceramic or stainless steel sinks, furniture such as tables, chairs, shelves, counters, windows, cookware, dishware and cutlery, tools such as surgical instruments, vacuum cleaners, machinery, pipelines, tanks and equipment for transport, processing and storage in food processing, for example rinse aids. Thus, the present invention further provides formulations, especially cosmetic or pharmaceutical formulations and care and cleaning formulations for use in the domestic and industrial sector, comprising inventive quaternary dialkanolamine esters and/or quaternary dialkanolamine esters obtainable by the process according to the invention and/or at least one inventive composition, especially in an amount of 0.1 to 7% by weight, preferably 0.5 to 4% by weight and more preferably 1 to 3% by weight, based on the overall formulation, especially aqueous formulations which preferably have a pH of 3.5 to 5.5.

The specified 0.1 to 7% by weight, preferably 0.5 to 4% by weight and more preferably 1 to 3% by weight present in the formulation are determined by adding up all components actually present in the inventive formulation (inventive quaternary dialkanolamine esters, quaternary dialkanolamine esters obtainable by the process according to the invention and inventive composition).

Preferred inventive formulations do not comprise any further alkyldialkanolamine esters.

The term "aqueous" in this context is understood to mean a water content of greater than 50% by weight and preferably greater than 75% by weight, based on the overall formulation.

Preferred inventive formulations are cosmetic haircare and skincare formulations, especially haircare formulations. Formulations particularly preferred in accordance with the invention are therefore hair shampoos, hair rinses, hair-setting agents, blow-dry setting agents, haircare emulsions, hair tonics, aerosol foams, hair-coloring compositions and blow-dry lotions.

The inventive formulations may comprise, for example, at least one additional component selected from the group of the
emollients,
coemulsifiers,
thickeners/viscosity regulators/stabilizers,
antioxidants,
hydrotropes (or polyols),
solids and fillers, pearlescent additives,
active deodorant and antiperspirant ingredients,
insect repellents,
self-tanning agents,
preservatives,
conditioners,
perfumes,
dyes,
active cosmetic ingredients,
care additives, superfatting agents,
solvents.

Substances which can be used as illustrative representatives of the individual groups are known to those skilled in the art and can be found, for example, in German application DE 102008001788.4. This patent application is hereby incorporated by reference and is therefore considered to form part of the disclosure.

With regard to further optional components and the amounts of these components used, reference is made exclusively to the relevant handbooks known to those skilled in the art, for example K. Schrader, "Grundlagen and Rezepturen der Kosmetika" [Cosmetic bases and formulations], $2^{nd}$ edition, pages 329 to 341, Huthig Buch Verlag Heidelberg.

The amounts of the respective additives are guided by the intended use.

Typical boundary formulations for the respective applications are known prior art and are included, for example, in the manufacturer brochures for the respective bases and active ingredients. These existing formulations can generally be adopted unchanged. If required, for adjustment and optimization, however, the desired modifications can be undertaken by simple tests without complication.

The present invention further provides for the use of the quaternary dialkanolamine esters and/or of the quaternary dialkanolamine esters obtainable by the process according to the invention and/or of at least one inventive composition and/or of at least one inventive formulation as a care composition, especially as a Skincare and haircare composition, and/or for conditioning of hair, and/or as a fabric softener.

The term "care composition" is understood here to mean a substance which fulfills the purpose of preserving an article in its original form, of reducing or of avoiding the effects of external influences (for example time, light, temperature, pressure, soiling, chemical reactions with other reactive compounds which come into contact with the article) for example aging, soiling, material fatigue, bleaching, or even to improve desired positive properties of the article. One example of the latter point is improved hair shine or greater elasticity of the article in question.

The examples adduced below describe the present invention by way of example, without any intention to restrict the invention, the range of application of which is evident from the overall description and the claims, to the embodiments cited in the examples.

All concentrations in the use examples are reported in percent by weight. For production of the formulations, customary formulation processes known to those skilled in the art were used.

The following figures form part of the examples.

EXAMPLES

Example 1

Preparation of Inventive Compound 1

A mixture of 179.5 g (0.89 mol) of lauric acid, 251.4 g (0.89 mol) of oleic acid and 619 g (1.795 mol) of behenic acid is homogenized at 70° C. in a flask with mechanical stirrer, column and distillation apparatus. Under a nitrogen atmosphere, 223.5 g (1.875 mol) of methyldiethanolamine are added dropwise and the mixture is gradually heated to 190° C. Water of reaction is distilled off continuously. 2 h after attainment of the target temperature, vacuum is applied and the reaction mixture is stirred at 190° C. for a further 3 h. The acid number is 3.1 mg KOH/g and the reaction mixture is cooled to 60° C. 771.4 g (1.2 mol) of the above-described diester are mixed with 448 g of C16-18 fatty alcohol, and 73.5 g (1.46 mol) of methyl chloride are added in portions in a pressure vessel at 80-110° C., such that the maximum pressure does not exceed 5 bar. After 5 h, the reaction mixture is analyzed, the total amine number is 2.9 mg KOH/g, the pressure is released gradually, and the excess methyl chloride is distilled off under reduced pressure. The active content of the finished product is 0.93 meq/g; the melting point is determined to be 58° C.

Example 2

Preparation of Inventive Compound 2

A mixture of 60.1 g (0.3 mol) of lauric acid, 196.0 g (0.7 mol) of oleic acid and 362.1 g (1.05 mol) of behenic acid is homogenized in a flask with mechanical stirrer, column and distillation apparatus. Under a nitrogen atmosphere, 119.2 g (1.0 mol) of methyldiethanolamine are added dropwise and the mixture is heated gradually to 190° C. Water of reaction is distilled off continuously. 2 h after attainment of the target temperature, vacuum is applied and the reaction mixture is stirred at 190° C. for a further 3 h. The acid number is 13.6 mg KOH/g, and the reaction mixture is cooled to 60° C.

701.0 g (1.0 mol) of the above-described diester are mixed with 404 g of C16-18 fatty alcohol, and 75.8 g (1.5 mol) of methyl chloride are added in portions in a pressure vessel at 80-110° C., such that the maximum pressure does not exceed 5 bar. After 5 h, the reaction mixture is analyzed, the total amine number is 3.1 mg KOH/g, the pressure is gradually released and the excess methyl chloride is distilled off under reduced pressure. The active content of the finished product is 0.86 meq/g; the melting point is determined to be 52° C.

Example 3

Testing of Hair Treatment Compositions Using the Inventive Compounds: Example 1 and Example 2

For the performance assessment, hair tresses which had been damaged beforehand in a standardized manner by a bleach treatment were used. For this purpose, standard hairdresser products are used. The damage to the hair tresses is described in detail in DE10327871.

For the performance assessment, the inventive compounds example 1 and example 2 were used in a simple cosmetic formulation.

The reference compounds used were the commercially available alkyl quat Behentrimonium Chloride (INCI) (VARISOFT® BT 85 pellets, Evonik Goldschmidt GmbH) and the commercially available Ester quat Distearoylethyl Dimonium Chloride (INCI) (VARISOFT® EQ 65 pellets, Evonik Goldschmidt GmbH).

The application properties in the case of use in hair rinses were tested in the following formulations (Tab. 1):

TABLE 1

Hair rinse formulations for testing of the hair-conditioning properties

| Formulation examples | C0a | 1a | 2a | V3a | V4a |
|---|---|---|---|---|---|
| TEGINACID ® C, Evonik Goldschmidt GmbH (INCI: Ceteareth-25) | 0.5% | 0.5% | 0.5% | 0.5% | 0.5% |
| TEGO ® Alkanol 16, Evonik Goldschmidt GmbH (INCI: Cetyl Alcohol) | 4% | 4% | 4% | 4% | 4% |
| Example 1 (65% strength in C16 fatty alcohol) | — | 2.3% | — | — | — |
| Example 2 (65% strength in C16 fatty alcohol) | — | — | 2.3% | — | — |
| VARISOFT ® EQ 65 pellets, 65% strength in C16 fatty alcohol, Evonik Goldschmidt GmbH (INCI: Distearoylethyl Dimonium Chloride, Cetearyl Alcohol) | — | — | — | 2.3% | — |
| VARISOFT ® BT 85, 85% strength isopropanol, Evonik Goldschmidt GmbH (INCI: Behentrimonium Chloride) | — | — | — | — | 1.76% |
| Water, demineralized | ad 100.0 | | | | |
| Citric acid | ad pH 4.0 | | | | |

To avoid influencing of the test results by formulation constituents (which are normally present), the chosen composition of the test formulations is deliberately simple. Inventive formulations may, as well as the ingredients mentioned and/or instead of the ingredients mentioned, also contain further ingredients. Especially the combination with further ingredients can lead to a synergistic improvement in the effects described.

The hair is pretreated by a shampoo formulation (Tab. 2) which does not contain any conditioner.

TABLE 2

Shampoo formulation for the pretreatment of the hair tresses

| Texapon NSO ®, 28% strength, Cognis (INCI: Sodium Laureth Sulfate) | 42.9% |
|---|---|
| NaCl | 3% |
| Water, demineralized | ad 100.0 |

Standardized Treatment of Pre-Damaged Hair Tresses with Conditioning Samples:

The hair tresses pre-damaged as described above are washed with the shampoo formulation from Tab. 2. This is done by wetting the hair tresses under flowing hot water. The excess water is pressed out gently by hand, then the shampoo is applied and incorporated gently into the hair for 1 min (0.5 ml/2 g of hair tress). The hair tress is rinsed under flowing hot water for 30 s. This procedure is repeated once more, except that the final rinse is for 1 min.

Subsequently, directly after washing, the hair tresses are conditioned with the hair rinse formulations from Tab. 1. This is done by applying the rinse and incorporating it gently into the hair (0.5 ml/2 g of hair tress). After a dwell time of 1 min, the hair is rinsed for a) 1 min or b) 3 min.

Prior to the sensory assessment, the hair is dried under air at 50% air humidity and 25° C. for at least 12 h.

Assessment Criteria:

The sensory assessments are made by grades which are awarded on a scale from 1 to 5, 1 being the worst and 5 the best rating. The individual test criteria each receive a separate assessment.

The Test Criteria are:

Wet combability, wet feel, dry combability, dry feel, appearance/shine.

In the tables which follow, the results of the sensory assessment of the treatment, conducted as described above, of the hair tresses with a) rinse time 1 min and b) rinse time 3 min are compared with the inventive formulations 1a and 2a, comparative formulations V3a and V4a, and the control formulation C0a (control without test substance).

a) Rinse time 1 min

TABLE 3

Results of the conditioning of hair with rinse time 1 min

| | Wet combability | Wet feel | Dry combability | Dry feel |
|---|---|---|---|---|
| Inventive formulation 1a | 4.6 | 4.7 | 4.7 | 4.6 |
| Inventive formulation 2a | 4.7 | 4.6 | 4.6 | 4.7 |
| Comparative formulation V3a (noninventive) | 4.5 | 4.5 | 4.6 | 4.6 |
| Comparative formulation V4a (noninventive) | 4.6 | 4.5 | 4.5 | 4.5 |
| Control formulation C0a (placebo) | 2.0 | 1.5 | 2.8 | 3.3 | b) Rinse time 3 min

TABLE 4

Results of the conditioning of hair with rinse time 3 min

| | Wet combability | Wet feel | Dry combability | Dry feel |
|---|---|---|---|---|
| Inventive formulation 1a | 4.0 | 4.2 | 4.4 | 4.4 |
| Inventive formulation 2a | 4.2 | 4.1 | 4.2 | 4.3 |
| Comparative formulation V3a (noninventive) | 3.5 | 3.4 | 3.4 | 3.6 |
| Comparative formulation V4a (noninventive) | 3.9 | 4.0 | 4.0 | 4.2 |
| Control formulation C0a (placebo) | 1.6 | 1.4 | 2.9 | 3.2 |

The results in table 3 show that the inventive formulations 1a and 2a with rinse time 1 min have very good conditioning properties, like comparative formulations V3a and V4a. As expected, comparative formulations V3a and V4a have similarly conditioning properties with rinse time 1 min.

The results in table 4 show that the inventive formulations 1a and 2a with rinse time 3 min have better conditioning properties than the comparative formulation V4a. The comparative formulation V4a contains, as a conditioning compound, VARISOFT® BT 85 (85% strength in isopropanol, Evonik Goldschmidt GmbH, INCI: Behentrimonium Chloride), an alkyl quat known for its very good conditioning properties even in the case of long rinse times.

Comparative formulation V3a contains, as a conditioning compound, VARISOFT® EQ 65 pellets (65% strength in C16 fatty alcohol, Evonik Goldschmidt GmbH, INCI: Distearoylethyl Dimonium Chloride, Cetearyl Alcohol), an ester quat which has very good conditioning properties with rinse time 1 min (see Tab. 3), but much poorer conditioning than the inventive ester quats Examples 1 and 2 with rinse time 3 min.

Example 4

Influence Of the Inventive Compounds on Combing Forces for Hair

Test conditions:
Measuring instrument: Diastron MTT 175
Measurement distance: 20 cm
Comb speed: 2000 ram/min
Hair tresses used: length=23 cm; width=1.5 cm; weight=2 g
Measurement conditions: T=22° C. The hair tresses are analyzed with a residual moisture content of 60%, determined by weight determination.

For the experiments, undamaged dark brown European hair is used. To conduct the combing force measurements, this hair is damaged in the laboratory by a permanent wave under standard conditions:

1.) 4 g of permanent wave solution/g of hair, contact for 15 min, rinsing for 2 min under flowing tap water (T=35° C.) (Permanent wave solution: universal permanent wave, Basler)

2.) 4 g of fixative (1 part fixing solution 3 parts water)/g of hair, contact for 10 min, rinsing for 2 min.
(Fixative solution: foam fixing concentrate, Basler)

Performance of the comb force measurement prior to the treatment with the test formulation:

The pre-damaged hair tresses are subjected to controlled climatic conditions overnight.

3.) The hair tress is dipped in a buffer solution (sodium citrate, pH=6) for 1 min.

4.) The hair tress is pre-combed by hand until no change in the comb resistance is found.

5.) The hair tress is secured in the measuring instrument and the first combing force measurement is conducted. The measurement is repeated a total of 10 times.

Treatment of the Tresses:

For each hair tress, 0.5 g of the respective test formulation is used (2 g of hair/0.5 g of solution). The formulation is massaged into the hair for 30 sec and then left for 5 min, then rinsed off under flowing tap water for 1 min or 3 min.

Performance of the combing force measurement after the treatment with the test formulation:
Points 3-5 are repeated.

Subsequently, the combing work (%) before and after the treatment with the test formulation is calculated.

Test Formulations Used:

The combing forces in the case of use in hair rinses were tested in the following formulations (Tab. 5):

TABLE 5

Hair rinse formulations for testing of the hair-conditioning properties

| Formulation examples | C0b | 1b | 2b | V3b | V4b |
|---|---|---|---|---|---|
| TEGINACID ® C, Evonik Goldschmidt GmbH (INCI: Ceteareth-25) | 0.5% | 0.5% | 0.5% | 0.5% | 0.5% |
| TEGO ® Alkanol 16, Evonik Goldschmidt GmbH (INCI: Cetyl Alcohol)) | 4% | 4% | 4% | 4% | 4% |
| Example 1 (65% strength in C16 fatty alcohol) | — | 1.5% | — | — | — |
| Example 2 (65% strength in C16 fatty alcohol) | — | — | 1.5% | — | — |
| VARISOFT ® EQ 65 pellets, 65% strength in C16 fatty alcohol, Evonik Goldschmidt GmbH (INCI: Distearoylethyl Dimonium Chloride, Cetearyl Alcohol) | — | — | — | 1.5% | — |
| VARISOFT ® BT 85, 85% strength in isopropanol, Evonik Goldschmidt GmbH (INCI: Behentrimonium Chloride) | — | — | — | — | 1.18% |
| Water, demineralized | ad 100.0 | | | | |
| Citric acid | ad pH 4.0 | | | | |

Figure 1:
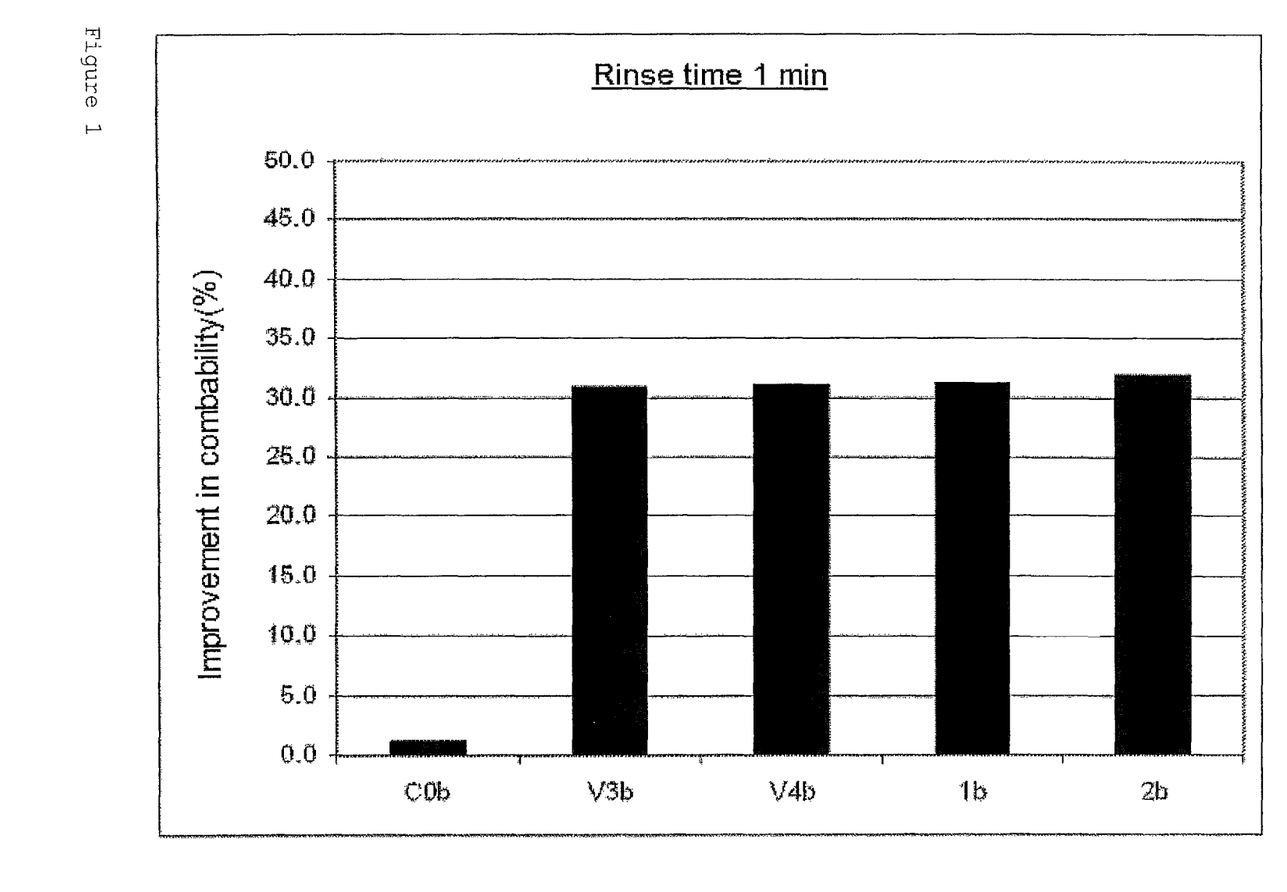
FIG. 1: Results of the combing force measurements with rinse time 1 min
Figure 2:
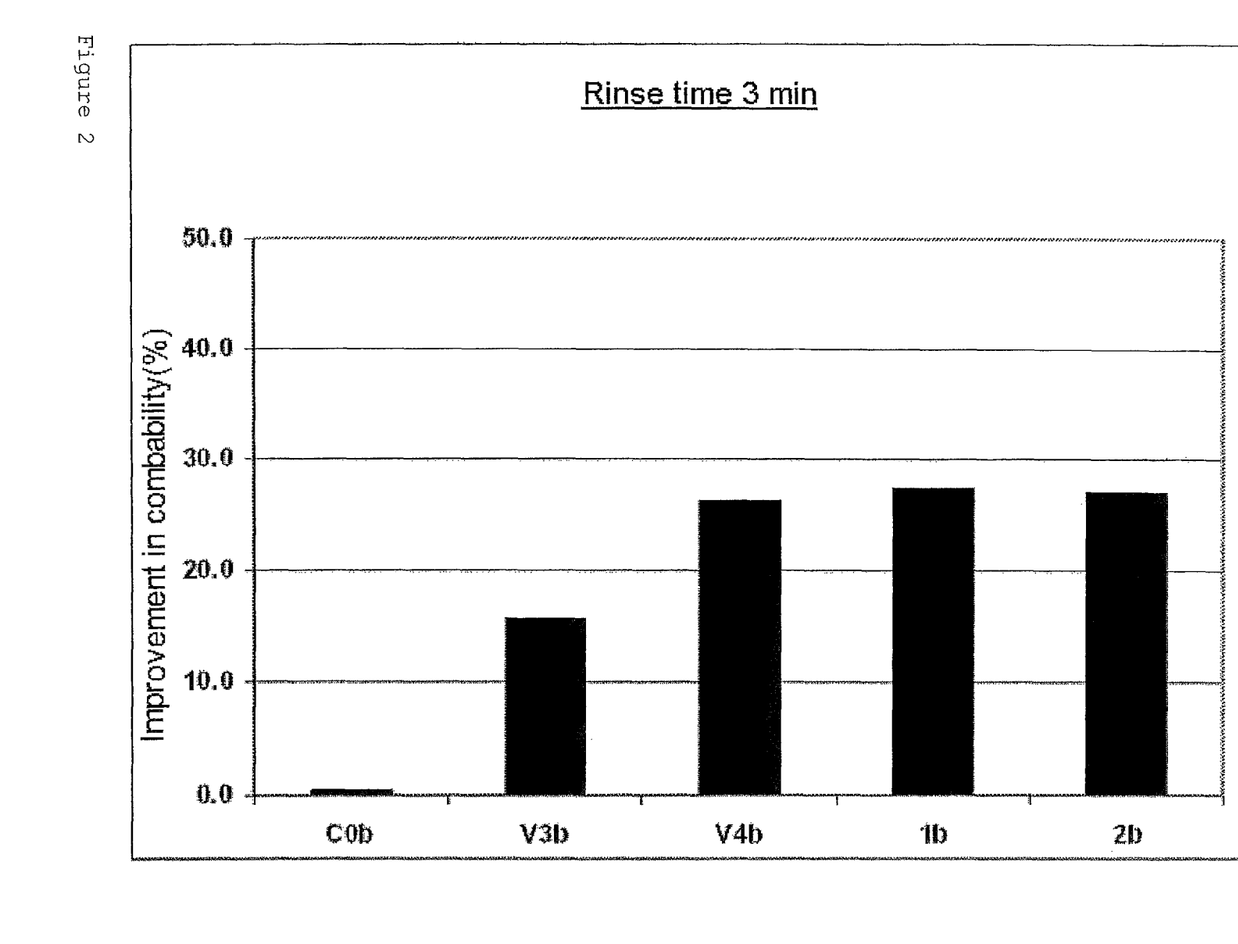
FIG. 2: Results of the combing force measurements with rinse time 3 min

The figure which follows compares the results of the combing force measurements of the experiments conducted as described above with a) rinse time 1 min and with b) rinse time 3 min using the inventive formulations 1b and 2b, the comparative formulations V3b and V4b and the control formulation C0b (control without test substance).

The results in FIG. 1 show that the inventive formulations 1b and 2b with rinse time 1 min have a marked reduction in the combing forces, like comparative formulations V3b and V4b. As expected, comparative formulations V3b and V4b generate a similarly marked reduction in the combing forces with rinse time 1 min.

The results in FIG. 2 show that inventive formulations 1b and 2b with rinse time 3 min have to a greater reduction in the combing forces than comparative formulation V4b. Comparative formulation V4b contains, as a conditioning compound, VARISOFT® BT 85 (85% strength in isopropanol, Evonik Goldschmidt GmbH, INCI: Behentrimonium Chloride), an alkyl quat known for its significant reduction of combing forces even with long rinse times.

Comparative formulation V3a contains, as a conditioning compound, VARISOFT® EQ 65 pellets (65% strength in C16 fatty alcohol, Evonik Goldschmidt GmbH, INCI: Distearoylethyl Dimonium Chloride, Cetearyl Alcohol), an ester quat which has good reduction of the combing forces with rinse time 1 min (see FIG. 2), but much poorer reduction of the combing forces than the inventive ester quats examples 1 and 2 with rinse time 3 min.

Formulation Examples

These formulation examples show that the inventive quaternary compounds can be used in a multitude of cosmetic formulations.

Formulation Example 1

Pearlized Shampoo

| | |
|---|---|
| TEXAPON ® NSO, Cognis. 28% strength (INCI: Sodium Laureth Sulfate) | 32.25% |
| Inventive example 1 | 0.25% |
| Perfume | 0.25% |
| Water | 55.25% |
| TEGO ® Detain F 50, Evonik Goldschmidt GmbH, 38% strength (INCI: Cocamidopropyl Betaine) | 8.00% |
| TEGO ® Pearl N 300 Evonik Goldschmidt GmbH (INCI: Glycol Distearate; Laureth-4; Cocamidopropyl Betaine) | 2.00% |

Formulation Example 2

Rinse-Off Conditioner

| | |
|---|---|
| Water | 92.0% |
| TEGINACID ® C, Evonik Goldschmidt GmbH | 0.5% |
| (INCI: Ceteareth-25) | |
| Inventive example 1 | 2.50% |
| TEGO ® Alkanol 1618, Evonik Goldschmidt GmbH | 5.00% |
| (INCI: Cetearyl Alcohol) | |
| Preservative, Perfume | q.s. |

Formulation Example 3

Rinse-Off Conditioner

| | |
|---|---|
| Water | 91.0% |
| Inventive example 2 | 2.00% |
| VARISOFT ® BT 85, Evonik Goldschmidt GmbH | 2.00% |
| (INCI: Behentrimonium Chloride) | |
| TEGO ® Alkanol 1618, Evonik Goldschmidt GmbH | 5.00% |
| (INCI: Cetearyl Alcohol) | |
| Preservative, Perfume | q.s. |

Formulation Example 4

Rinse-Off Conditioner

| | |
|---|---|
| Water | 90.20% |
| Inventive example 1 | 2.00% |
| VARISOFT ® EQ 65, Evonik Goldschmidt GmbH | 2.00% |
| (INCI: Distearoyl Dimonium Chloride, Cetearyl Alcohol) | |
| TEGO ® Alkanol 1618, Evonik Goldschmidt GmbH | 5.80% |
| (INCI: Cetearyl Alcohol) | |
| Preservative, Perfume | q.s. |

Formulation Example 5

Rinse-Off Conditioner

| | |
|---|---|
| Water | 89.20% |
| TEGINACID ® C, Evonik Goldschmidt GmbH | 0.5% |
| (INCI: Ceteareth-25) | |
| VARISOFT ® EQ 65, Evonik Goldschmidt GmbH | 2.00% |
| (INCI: Distearoyl Dimonium Chloride, Cetearyl Alcohol) | |
| Inventive example 1 | 2.00% |
| ABIL ® Quat 3272, Evonik Goldschmidt GmbH | 1.30% |
| (INCI: Quaternium-80) | |
| TEGO ® Alkanol 1618, Evonik Goldschmidt GmbH | 5.00% |
| (INCI: Cetearyl Alcohol) | |
| Preservative, Perfume | q.s. |

Formulation Example 6

Rinse-Off Conditioner

| | |
|---|---|
| TEGINACID ® C, Evonik Goldschmidt GmbH | 0.50% |
| (INCI: Ceteareth-25) | |
| TEGO ® Alkanol 16, Evonik Goldschmidt GmbH | 2.00% |
| (INCI: Cetyl Alcohol) | |
| TEGO ® Amid S 18, Evonik Goldschmidt GmbH | 1.00% |
| (INCI: Stearamidopropyl Dimethylamine) | |
| Inventive example 1 | 1.50% |
| Propylene Glycol | 2.00% |
| Citric Acid Monohydrate | 0.30% |
| Water | 92.70% |
| Preservative, Perfume | q.s. |

Formulation Example 7

Rinse-Off Conditioner

| | |
|---|---|
| TEGINACID ® C, Evonik Goldschmidt GmbH | 0.50% |
| (INCI: Ceteareth-25) | |
| TEGO ® Alkanol 16, Evonik Goldschmidt GmbH | 5.00% |
| (INCI: Cetyl Alcohol) | |
| TEGOSOFT ® DEC, Evonik Goldschmidt GmbH | 1.00% |
| (INCI: Diethylhexyl Carbonate) | |
| Inventive example 2 | 1.50% |
| Water | 89.20% |
| TEGO ® Cosmo C 100 Evonik Goldschmidt GmbH | 0.50% |
| (INCI: Creatine) | |
| Propylene Glycol | 2.00% |
| Citric Acid Monohydrate | 0.30% |
| Preservative, Perfume | q.s. |

Formulation Example 8

Leave-in Conditioner Spray

| | |
|---|---|
| Lactic Acid, 80% | 0.40% |
| Water | 95.30% |
| Inventive example 1 | 1.20% |
| TEGIN ® G 1100 pellets, Evonik Goldschmidt GmbH | 0.60% |
| (INCI: Glycol Distearate) | |
| TEGO ® Care PS, Evonik Goldschmidt GmbH | 1.20% |
| (INCI: Methyl Glucose Sesquistearate) | |
| TEGOSOFT ® DEC, Evonik Goldschmidt GmbH | 1.30% |
| (INCI: Diethylhexyl Carbonate) | |
| Preservative, Perfume | q.s. |

-continued (from previous page):

| | |
|---|---|
| ANTIL ® 171 Evonik Goldschmidt GmbH | 1.50% |
| (INCI: PEG-18 Glyceryl Oleate/Cocoate) | |
| NaCl | 0.50% |
| Preservative | q.s. |

Formulation Example 9

Leave-in Conditioner Spray

| | |
|---|---|
| Lactic Acid, 80% | 0.40% |
| Water | 95.30% |
| TEGO ® Amid S 18, Evonik Goldschmidt GmbH (INCI: Stearamidopropyl Dimethylamine) | 1.20% |
| Inventive example 1 | 0.30% |
| TEGIN ® G 1100 pellets, Evonik Goldschmidt GmbH (INCI: Glycol Distearate) | 0.90% |
| TEGO ® Care PS, Evonik Goldschmidt GmbH (INCI: Methyl Glucose Sesquistearate) | 1.60% |
| TEGOSOFT ® DEC, Evonik Goldschmidt GmbH (INCI: Diethylhexyl Carbonate) | 0.30% |
| Preservative, Perfume | q.s. |

Formulation Example 10

Leave-in Conditioner Spray

| | |
|---|---|
| TAGAT ® CH-40, Evonik Goldschmidt GmbH (INCI: PEG-40 Hydrogenated Castor Oil) | 2.20% |
| Ceramide VI, Evonik Goldschmidt GmbH (INCI: Ceramide 6 II) | 0.05% |
| Perfume | 0.20% |
| Water | 90.95% |
| Inventive example 1 | 0.30% |
| LACTIL ® Evonik Goldschmidt GmbH (INCI: Sodium Lactate; Sodium PCA; Glycine; Fructose; Urea; Niacinamide; Inositol; Sodium benzoate; Lactic Acid) | 2.00% |
| TEGO ® Betain F 50 Evonik Goldschmidt GmbH 38% (INCI: Cocamidopropyl Betaine) | 2.30% |
| Citric Acid (10% in water) | 2.00% |

Formulation Example 11

Leave-in Conditioner Foam

| | |
|---|---|
| Inventive example 1 | 0.30% |
| TAGAT ® CH-40, Evonik Goldschmidt GmbH (INCI: PEG-40 Hydrogenated Castor Oil) | 1.0% |
| Perfume | 0.30% |
| TEGO ® Betain 810, Evonik Goldschmidt GmbH (INCI: Capryl/Capramidopropyl Betaine) | 2.00% |
| Water | 94.00% |
| TEGO ® Cosmo C 100, Evonik Goldschmidt GmbH (INCI: Creatine) | 0.50% |
| TEGOCEL ® HPM 50, Evonik Goldschmidt GmbH (INCI: Hydroxypropyl Methylcellulose) | 0.30% |
| VARISOFT ® 300, Evonik Goldschmidt GmbH (INCI: Cetrimonium Chloride) | 1.0% |
| LACTIL ® Evonik Goldschmidt GmbH (INCI: Sodium Lactate; Sodium PCA; Glycine; Fructose; Urea; Niacinamide; Inositol; Sodium benzoate; Lactic Acid) | 0.50% |
| Citric Acid, 30% | 0.10% |
| Preservative | q.s. |

Formulation Example 12

Strong Hold Styling Gel

| | |
|---|---|
| TEGO ® Carbomer 141, Evonik Goldschmidt GmbH (INCI: Carbomer) | 1.20% |
| Water | 66.70% |
| NaOH, 25% | 2.70% |
| PVP/VA W-735, ISP (INCI: PVP/VA Copolymer) | 16.00% |
| Inventive example 1 | 0.30% |
| Alcohol Denat. | 10.50% |
| TAGAT ® O 2 V, Evonik Goldschmidt GmbH (INCI: PEG-20 Glyceryl Oleate) | 2.00% |
| Perfume | 0.30% |
| ABIL ® B 88183, Evonik Goldschmidt GmbH (INCI: PEG/PPG-20/6 Dimethicone) | 0.30% |
| Preservative | q.s. |

Formulation Example 13

Bodycare Composition

| | |
|---|---|
| TEXAPON ® NSO, Cognis, 28% strength (INCI: Sodium Laureth Sulfate) | 30.00% |
| TEGOSOFT ® PC 31, Evonik Goldschmidt GmbH (INCI: Polyglyceryl-3 Caprate) | 0.70% |
| Inventive example 2 | 0.30% |
| Perfume | 0.30% |
| Water | 53.90% |
| TEGOCEL ® HPM 4000, Evonik Goldschmidt GmbH (INCI: Hydroxypropyl Methylcellulose) | 0.30% |
| REWOTERIC ® AM C, Evonik Goldschmidt GmbH, 32% strength (INCI: Sodium Cocoamphoacetate) | 10.00% |
| Citric Acid Monohydrate | 0.50% |
| REWODERM ® LI S 80, Evonik Goldschmidt GmbH (INCI: PEG-200 Hydrogenated Glyceryl Palmate; PEG-7 Glyceryl Cocoate) | 2.00% |
| TEGO ® Pearl N 300, Evonik Goldschmidt GmbH (INCI: Glycol Distearate; Laureth-4; Cocamidopropyl Betaine) | 2.00% |

Formulation Example 14

Mild Foam Bath

| | |
|---|---|
| TEXAPON ® NSO, Cognis, 28% strength (INCI: Sodium Laureth Sulfate) | 27.00% |
| REWOPOL ® SB FA 30, Evonik Goldschmidt GmbH. 40% strength (INCI: Disodium Laureth Sulfosuccinate) | 12.00% |
| TEGOSOFT ® LSE 65 K SOFT, Evonik Goldschmidt GmbH (INCI: Sucrose Cocoate) | 2.00% |
| Water | 39.00% |
| REWOTERIC ® AM C, Evonik Goldschmidt GmbH, 32% strength (INCI: Sodium Cocoamphoacetate) | 13.00% |
| Inventive example 2 | 0.40% |
| Citric Acid (30% in water) | 3.00% |
| ANTIL ® 171 Evonik Goldschmidt GmbH (INCI: PEG-18 Glyceryl Oleate/Cocoate) | 1.60% |
| TEGO ® Pearl N 300 Evonik Goldschmidt GmbH (INCI: Glycol Distearate; Laureth-4; Cocamidopropyl Betaine) | 2.00% |

Formulation Example 15

Rinse-Off Conditioner

| | |
|---|---|
| Water | 89.20% |
| Inventive example 2 | 3.00% |
| ABIL ® OSW 5, Evonik Goldschmidt GmbH (INCI: Cyclopentasiloxane; Dimethiconol) | 1.80% |
| TEGO ® Alkanol 1618, Evonik Goldschmidt GmbH (INCI: Cetearyl Alcohol) | 6.00% |
| Preservative, Perfume | q.s. |

Formulation Example 16

Rinse-Off Conditioner

| | |
|---|---|
| Water | 89.20% |
| TEGINACID ® C, Evonik Goldschmidt GmbH (INCI: Ceteareth-25) | 0.5% |
| VARISOFT ® EQ 65, Evonik Goldschmidt GmbH (INCI: Distearyl Dimonium Chloride, Cetearyl Alcohol) | 1.50% |
| Inventive example 2 | 2.00% |
| ABIL ® Soft AF 100, Evonik Goldschmidt GmbH (INCI: Methoxy PEG/PPG-7/3 Aminopropyl Dimethicone) | 1.00% |
| TEGO ® Alkanol 1618, Evonik Goldschmidt GmbH (INCI: Cetearyl Alcohol) | 5.80% |
| Preservative, Perfume | q.s. |

Formulation Example 17

Rinse-Off Conditioner

| | |
|---|---|
| Water | 91.50% |
| TEGINACID ® C, Evonik Goldschmidt GmbH (INCI: Ceteareth-25) | 0.5% |
| Inventive example 2 | 2.00% |
| SF 1708, Momentive (INCI: Amodimethicone) | 1.00% |
| TEGO ® Alkanol 1618, Evonik Goldschmidt GmbH (INCI: Cetearyl Alcohol) | 5.00% |
| Preservative, Perfume | q.s. |

Formulation Example 18

Fabric Softener 1

| | |
|---|---|
| Inventive example 1 | 4.00% |
| Dyestuff, 1% | 0.15% |
| Perfume | 0.20% |
| Water, demin. | 94% |

Formulation Example 19

Fabric Softener 2

| | |
|---|---|
| Inventive example 2 | 4.00% |
| Plantatex HCC | 5.00% |

| | |
|---|---|
| Glycerin (99.5% by weight) | 17.00% |
| Phenonip | 0.70% |
| Water, demin. | Ad 100% |

The invention claimed is:

1. A mixture of quaternary dialkanolamine esters of general formula (I)

formula (I)

where
Y$^1$ and Y$^2$ are the same or different and are each independently an alkyl radical having 1 to 6 carbon atoms, a benzyl radical or H,
n=1 to 4,
A- is an anion,
X$^1$ and X$^2$ are the same or different and are each independently selected from groups (a), (b), (c) and (d), said groups consisting of
  (a) acyl radicals containing 6 to 14 carbon atoms,
  (b) acyl radicals containing 15 to 20 carbon atoms and at least one carbon-carbon double bond,
  (c) acyl radicals containing 20 to 24 carbon atoms, and
  (d) acyl radicals which contain 3 to 28 carbon atoms and are not included in groups (a) to (c), or H,
with the proviso that each molecule of general formula (I) contains a numerical average of
  0.30 to 1.50 radicals from group (a),
  0.10 to 1.30 radicals from group (b),
  0.40 to 1.60 radicals from group (c),
  0 to 0.20 radical from group (d),
and the numerical averages per molecule of the radicals from groups (a), (b), (c) and (d) add up to 2.

2. The mixture of quaternary dialkanolamine esters as claimed in claim 1, wherein
acyl radicals from group (a) are selected from $C_5H_{11}CO—$, $C_7H_{15}CO—$, $C_9H_{19}CO—$, $C_{11}H_{23}CO—$ and $C_{13}H_{27}CO—$,
acyl radicals from group (b) are selected from $C_{15}H_{29}CO—$, $C_{17}H_{33}CO—$, $C_{17}H_{31}CO—$, $C_{17}H_{29}CO—$, $C_{19}H_{37}CO—$, $C_{19}H_{31}CO—$ and $C_{19}H_{29}CO—$,
acyl radicals from group (c) are selected from $C_{19}H_{39}CO—$, $C_{21}H_{43}CO—$ and $C_{23}H_{47}CO—$, and
acyl radicals from group (d) are selected from acyl radicals of the carboxylic acids which are additionally present in technical grade mixtures of the carboxylic acids which determine the acyl radical from groups (a), (b) and (c).

3. The mixture of quaternary dialkanolamine esters as claimed in claim 1, wherein
acyl radicals from group (a) are selected from $C_{11}H_{23}CO—$,
acyl radicals from group (b) are selected from $C_{15}H_{29}CO—$, $C_{17}H_{33}CO$, $C_{17}H_{31}CO—$, $C_{17}H_{29}CO—$ and $C_{19}H_{37}CO—$ in a weight ratio of 3-7:68-76:5-13:1-3:0-2,
acyl radicals from group (c) are selected from $C_{19}H_{39}CO—$, $C_{21}H_{43}CO—$, $C_{23}H_{47}CO—$ in a weight ratio of 4-8:85-99:0-3.

4. The mixture of quaternary dialkanolamine esters as claimed in claim 1, wherein the acyl radicals from groups (a) to (d) are determined via the acyl radicals of a mixture consisting of
technical grade lauric acid,
technical grade oleic acid, and
technical grade behenic acid.

5. The mixture of quaternary dialkanolamine esters as claimed in claim 1, wherein the numerical average of the molar ratio of the sum of acyl radicals from group (a) and group (b) to acyl radicals from group (c) is 1:0.67 to 4.

6. A process for preparing a mixture of quaternary dialkanolamine esters in accordance with claim 1, comprising the process steps of
A) reacting an alkyldialkanolamine in which the two alkanol groups are selected from the group consisting of —$CH_2OH$, —$C_2H_4OH$, —$C_3H_6OH$ and —$C_4H_8OH$ and the alkyl group is selected from the group consisting of alkyl radicals having 1-6 carbon atoms with a mixture of carboxylic acids consisting of
(e) carboxylic acid containing 6 to 14 carbon atoms,
(f) carboxylic acid containing 15 to 20 carbon atoms and at least one carbon-carbon double bond, and
(g) carboxylic acid containing 20 to 24 carbon atoms, and optionally
(h) carboxylic acid which contains 3 to 28 carbon atoms and is not included in groups (e), (f) and (g),
B) reacting the product from process step A) with a quaternizing agent selected from dialkyl sulfates, alkyl halides and benzyl halides, and/or
C) neutralizing the reaction mixture with an acid,
with the proviso that, based on all carboxylic acids from groups (e), (f), (g) and (h), 0 to 10 mol % of carboxylic acids from group (h) is used.

7. The process as claimed in claim 6, wherein, for each mole of alkyldialkanolamine used in process step (A),
0.30 to 1.50 mol of carboxylic acid from group (e),
0.10 to 1.30 mol of carboxylic acid from group (f), and
0.40 to 1.60 mol of carboxylic acid from group (g)
are used.

8. The process as claimed in claim 6, wherein, for each mole of alkyldialkanolamine, carboxylic acids from groups (e), (f), (g) and optionally (h) are used in a total amount of 1.80 to 2.5 mol.

9. The process as claimed in claim 6, wherein, in process step B), at least one solvent selected from the group consisting of short-chain alcohols, fatty alcohols, polyols and carbonates is used.

10. A composition comprising:
a mixture of quaternary dialkanolamine esters of general formula (I)

formula (I)

where
$Y^1$ and $Y^2$ are the same or different and are each independently an alkyl radical having 1 to 6 carbon atoms, a benzyl radical or H,
n=1 to 4,
A- is an anion,
$X^1$ and $X^2$ are the same or different and are each independently selected from groups (a), (b), (c) and (d), said groups consisting of
(a) acyl radicals containing 6 to 14 carbon atoms,
(b) acyl radicals containing 15 to 20 carbon atoms and at least one carbon-carbon double bond,
(c) acyl radicals containing 20 to 24 carbon atoms, and
(d) acyl radicals which contain 3 to 28 carbon atoms and are not included in groups (a) to (c), or H,
with the proviso that each molecule of the general formula (I) contains a numerical average of
0.30 to 1.50 radicals from group (a),
0.10 to 1.30 radicals from group (b),
0.40 to 1.60 radicals from group (c),
0 to 0.20 radical from group (d),
and the numerical averages per molecule of the radicals from groups (a), (b), (c) and (d) add up to 2, and at least one solvent.

11. The composition as claimed in claim 10, wherein the solvent is isopropanol or propylene carbonate.

12. A formulation comprising a mixture of quaternary dialkanolamine esters of general formula (I)

formula (I)

where
$Y^1$ and $Y^2$ are the same or different and are each independently an alkyl radical having 1 to 6 carbon atoms, a benzyl radical or H,
n=1 to 4,
A- is an anion,
$X^1$ and $X^2$ are the same or different and are each independently selected from groups (a), (b), (c) and (d), said groups consisting of
(a) acyl radicals containing 6 to 14 carbon atoms,
(b) acyl radicals containing 15 to 20 carbon atoms and at least one carbon-carbon double bond,
(c) acyl radicals containing 20 to 24 carbon atoms, and
(d) acyl radicals which contain 3 to 28 carbon atoms and are not included in groups (a) to (c), or H,
with the proviso that each molecule of general formula (I) contains a numerical average of
0.30 to 1.50 radicals from group (a),
0.10 to 1.30 radicals from group (b),
0.40 to 1.60 radicals from group (c),
0 to 0.20 radical from group (d),
and the numerical averages per molecule of the radicals from groups (a), (b), (c) and (d) add up to 2, and at least one solvent.

13. The quaternary dialkanolamine ester as claimed in claim 1, wherein said anion is selected from the group consisting of chloride, bromide, methyl sulfate, tosylate, phosphate, sulfate, hydrogen sulfate, lactate, acetate and citrate.

14. The formulation of claim 12, wherein the quaternary dialkanoline esters and/or said composition is present in an amount of 0.5 to 4% by weight, based on the overall formulation.

15. The formulation of claim 12, wherein the quaternary dialkanoline esters and/or said composition is present in an amount of 1-3% by weight, based on the overall formulation.

16. The formulation of claim 12, wherein said formulation is an aqueous formulation.

17. The formulation of claim 12, wherein said formulation has a pH of 3.5 to 5.

18. The formulation of claim 12, wherein said formulation is a cosmetic or pharmaceutical formulation and care and cleaning formulation for use in the domestic and industrial sector.

19. The formulation of claim 18, wherein said care and cleaning composition is a skin care composition, haircare composition and/or a fabric softener.

* * * * *